United States Patent [19]
Chang

[11] Patent Number: 5,220,636
[45] Date of Patent: Jun. 15, 1993

[54] ADJUSTABLE AIR FRESHENER

[75] Inventor: Charles Chang, 127 E. Edsall Ave., Palisades Park, N.J. 07650

[73] Assignee: Charles Chang, Palisades Park, N.J.

[21] Appl. No.: 804,941

[22] Filed: Dec. 11, 1991

[51] Int. Cl.⁵ .................. F24F 6/00; A61M 16/00
[52] U.S. Cl. ................................. 392/392; 392/390
[58] Field of Search ............... 392/390, 392, 403, 405

[56] References Cited

U.S. PATENT DOCUMENTS

| | | | |
|---|---|---|---|
| 3,748,438 | 7/1973 | Costello | 392/390 |
| 3,872,280 | 3/1975 | Van Dalen | 392/390 |
| 4,588,874 | 5/1986 | Napierski | 392/390 |

FOREIGN PATENT DOCUMENTS

| | | | |
|---|---|---|---|
| 2547734 | 12/1984 | France | 392/390 |
| 2547735 | 12/1984 | France | 392/390 |

OTHER PUBLICATIONS

Brown, W. W., "Automatic Disk Loader . . . ", IBM Tech. Disc. Bull., vol. 26, No. 6, Nov. 1983.

Primary Examiner—Teresa J. Walberg
Attorney, Agent, or Firm—Richard A. Joel

[57] ABSTRACT

An adjustable air freshener involves a container for a scented gel which includes a heater which is integrally molded within the base of the container with a connecting plug extending outwardly for coupling to an electrical outlet. The front portion of the container includes a rotary cover with a circular configuration having a solid dividing wall on half of the circle extending downwardly to block the flow of hot air from affecting the gel which is positioned between the base and cover within the container. The other half of the cover includes a plurality of spaced apertures which are positioned opposite the heated gel to provide a predetermined scent to the room. The cover and gel may be rotated with respect to the base in predetermined increments to provide the desired scent.

5 Claims, 2 Drawing Sheets

ADJUSTABLE AIR FRESHENER

BACKGROUND OF THE INVENTION

The prior art discloses various air fresheners including U.S. Pat. No. 4,544,592 to Spector which discloses an aroma generating capsule adhesively attached to the surface of an incandescent bulb. The capsule includes a plastic skin and a vent hole through which an aroma is forced into the atmosphere.

Of particular interest is U.S. Pat. No. 4,849,606 to Martens which is the same general area of art as the present invention. The Martens patent discloses a tamper-resistant container suitable for use with an electrically heated vapor dispensing apparatus. The container includes a packaged gel which is inserted into a dispensing apparatus having an inner wall with an integrally molded electrical plug and an outer wall having a plurality of openings through which the scented aroma is dispensed.

U.S. Pat. No. 4,571,485 discloses an electrically heated aromatic generator utilizing a replaceable aroma cube which is inserted into a well in the generator. U.S. Pat. No. 4,731,520 discloses an aroma diffuser assembly for dispensing a scent from a replaceable and expendable cartridge. A heater assembly is also provided to vaporize the cartridge liquid which exits through an aperture into the atmosphere.

The prior art also includes U.S. Pat. No. 4,837,421 which shows a fragrance dispensing apparatus which releases a fragrance from a solid polyamide resin. A heating resistor is provided to maintain an elevated temperature. Also of interest are U.S. Pat. No. 3,895,298 to Moran, U.S. Pat. No. 4,425,302 to Pons Pons and U.S. Pat. No. 4,804,821 to Glucksman.

The prior art does not disclose an adjustable air freshener of the type set forth herein which is inexpensive and easy to manufacture and use. In the present invention the aroma dispensing can be regulated to conform to the size of a room and waste can be minimized. The disadvantage of an overpowering scent present in the prior art is thus avoided. Further, the useful life of the gel is extended since all of the product is not continuously exposed to the heater at the same time in contrast to the Martens patent.

Certain factors influence the amount of fragrance released by an air freshener utilizing a heated gel including:

1. Temperature of the heating element or surface;
2. Surface area of contact between the gel and heated surface;
3. Time of contact;
4 Surface area of permeation (surface area of the film covering the gel);
5. Permeability of the film encapsulating the gel; and
6. The amount of the gel or oil fragrance, and
7. The flow of hot air.

In the present invention, factors 1, 4, 5, and 6 are fixed and factor 3 (time) starts from the moment of plug-in and continues until the gel is exhausted. The only factor over which control may be exerted without employing expensive regulating mechanisms is factor 2 (area of contact) and factor 7. The time factor can be regulated by an on-off switch, which is subject to human error, or by an automatic device set at a predetermined interval—both costly and affecting the size of the device. This invention proposes to regulate the scent from an air freshener or dispenser by controlling the area of contact between the heater and gel with a rotatable cover which cooperates with a unique base. The dial is rotated to place the scented gel in contact with the heated surface to produce the desired scent. A dividing wall across the center of the cover restricts the hot air affecting only the portion of gel which is moved up to the heated compartment. The portion of gel which remains in the cold compartment is protected from the contact of the hot air by the dividing wall.

SUMMARY OF THE INVENTION

The present invention comprises an adjustable air freshener which includes a unique container for a packaged scented gel with adjustment means for regulating the aroma produced by heating the gel. The container has a rear wall or base with an integrally molded electrical plug extending outwardly therefrom for connection to an electrical outlet and a heater such as a resistor also molded within said wall adjacent the gel.

Plugging in the container activates the heater causing the gel which is positioned opposite the heater to vaporize and issue a scent through openings in the front cover of the container. The front cover, in one embodiment comprises a circular rotatable dial having a solid portion and a gel portion having one or more apertures. The dial with the scented gel is rotated to move the gel into the heater compartment in order to supply a predetermined amount of aroma to the surrounding room. Indicia are provided to signal the amount of gel exposed to the heater. Thus the strength of the scent is controlled simply and inexpensively without complicated controls by moving the gel portion in predetermined increments opposite the heater.

Accordingly, an object of this invention is to provide a new and improved adjustable air freshener.

Another object of this invention is to provide a new and improved adjustable air freshener having integral heating means to vaporize a scented gel and means to regulate the scent by controlling the amount of gel positioned adjacent the heater.

A further object of this invention is to provide a new and improved air freshener having a rotary dial to regulate the amount of scent issuing therefrom by moving a packaged gel in predetermined increments with respect to an integral heater.

A more specific object of this invention is to provide a new and improved compartmentalized air freshener having adjustment means with predetermined apertures positioned adjacent an aromatic source and movable with respect to a heater in set increments to regulate the aroma issuing therefrom.

DETAILED DESCRIPTION OF THE DRAWINGS

The above and other objects and advantages of the current invention may be more clearly seen when viewed in conjunction with the accompanying drawings wherein.

Figure 9A:
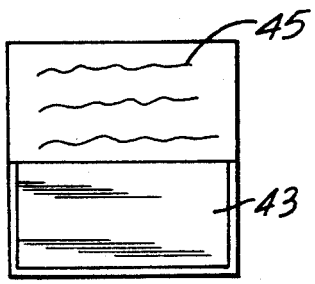
Figure 9B:
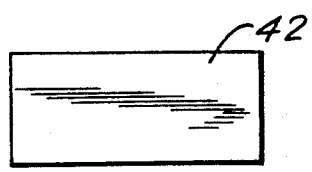

FIGS. 9A and 9B disclose an alternate sliding version of the invention; and

Figure 10:
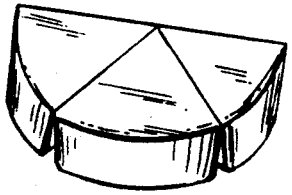

FIGS. 10a,b depict a typical gel package.

DETAILED DESCRIPTION OF THE INVENTION

Referring now to the drawings, the invention comprises an adjustable air freshener 10 which permits a predetermined amount of a scent to be released into the surroundings. The freshener 10 comprises a front cover 11 with downwardly extending side walls 12 and a base 13. The upper portion 14 of the base 13 is spaced from the lower portion 16 of the cover 11 to accomodate a scented gel package 17 therebetween at one end.

The base 13 comprises a heater 18 at one end adjacent the gel package 17. The heater 18 may comprise a resistive wire or resistance 15 which receives power from a brass plug 19 which projects outwardly from the heater 18 for insertion directly into a conventional wall outlet (not shown) without the need for a switch which would add to the cost.

The cover 11 also includes a downwardly extending central member or wall 21 which rests on the base 13. The cover 11 is rotatable about the center of said member 21. The base comprises a circular upper surface 14 with a downwardly extending skirt or wall 22 and an upwardly extending wall 25 which are retained within the cover 12 by inward projections 23 on the downwardly extending wall 12 of the cover 11. To separate the base 13 from the cover 11, the flexible wall 12 is merely moved outwardly to permit the base 13 to be withdrawn.

Figure 1:
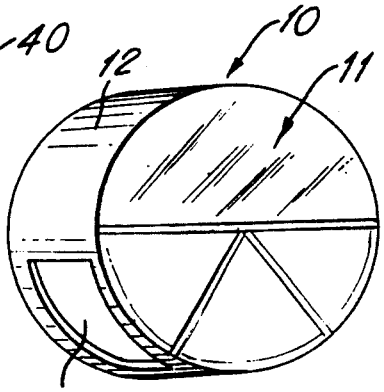
FIG. 1 is a perspective view of the cover for the invention.
Figure 1A:
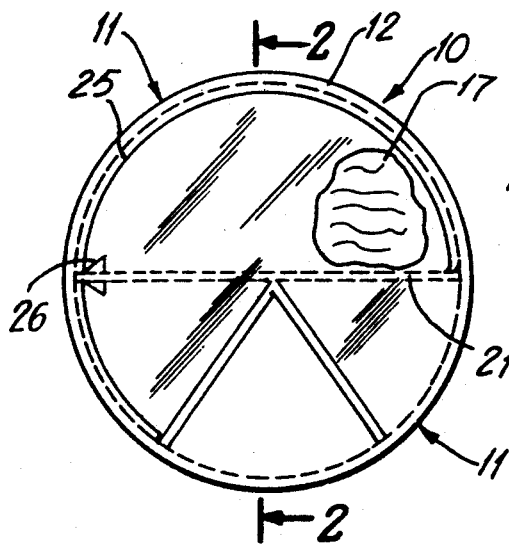
FIG 1A is a top view of the cover for the invention with portions shown in phantom and portions broken away to more clearly illustrate the invention.
Figure 4:
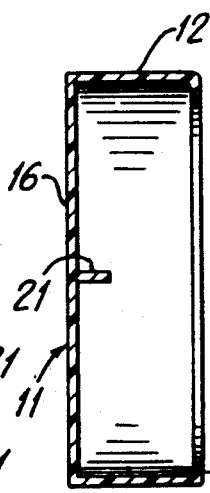
FIG. 4 is a crossectional view of the cover.
Figure 2:
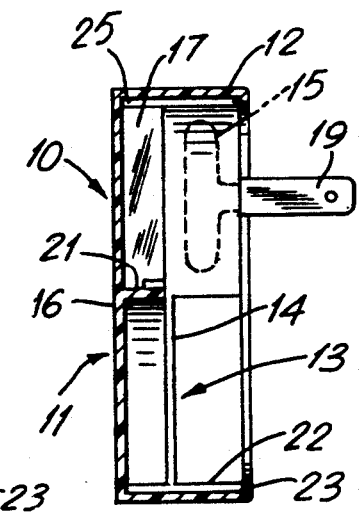
FIG. 2 is a view of the invention taken along the line 2—2 of the invention as shown in FIG 1A.

In order to provide indicia for strength of odor or usage without expensive instrumentation, several options are provided. Firstly, a clear see-through cover 11 could be provided for actual viewing. Secondly, as shown in FIG 1A, a cover 11 with the top half totally hollow or open could be provided and, thirdly, a cover 11 with arrows 26 serving as indicia could be provided.

Figure 5:
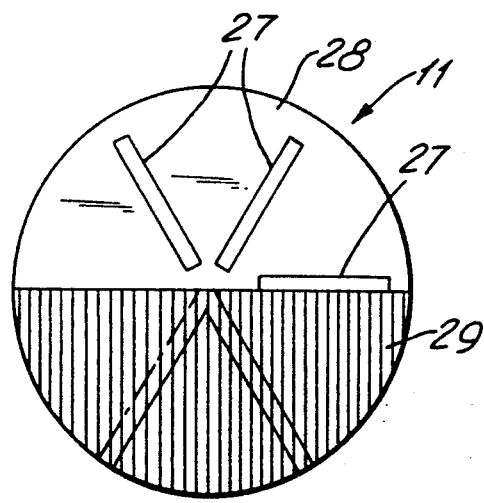
FIG. 5 is a top view of an alternate embodiment of the invention with open indicator slots in the cover cooperating with a colored base.

In a further embodiment (FIG. 5) three evenly spaced open slots 27 are provided on the top half 28 of the rotatable cover 12. For every one-third turn, one slot 27 will move to the bottom half 29. The bottom surface 32 is colored to provide an indication of odor strength. For example, one colored slot 27 would mean ⅓ of "strength." Three colored slots 27 would mean full strength or no reserved gel.

Figure 6:
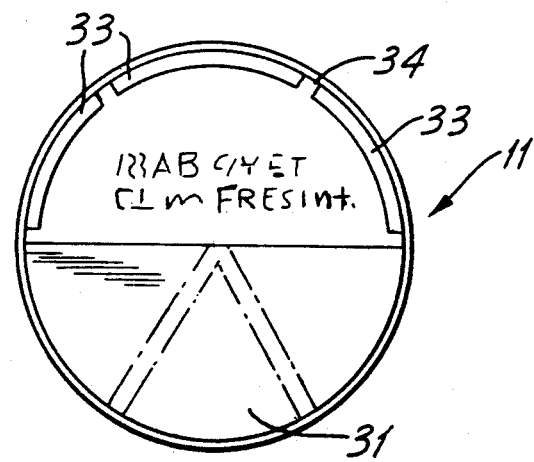
FIG. 6 is a top view of a further embodiment of the invention showing peripheral slots in the cover.

In the embodiment of FIG. 6, the same concepts are used except that three open slots 33 are located about the periphery of the cover 12. Bottom half openings 31 are also provided. This arrangement provides space 34 for a logo or decoration on the top half.

Figure 7:
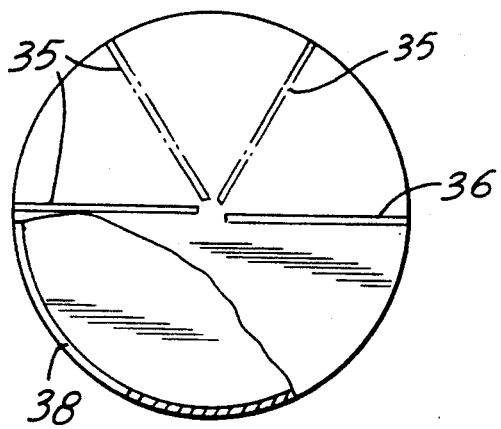
FIG. 7 is a top view of the base cooperating with the covers of FIGS. 5 and 6.
Figure 7A:
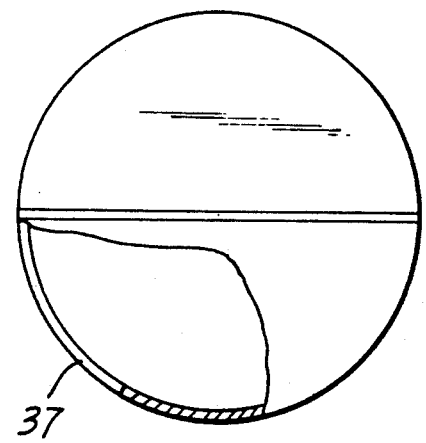

The base 13 as shown in FIG. 7, includes a low bump or "stop" 35 for each ⅓ turn of the cover 11 and a high bump 36 spaced at one end working in conjunction with 21 to prevent the overturn of the cover 12 and signify maximum exposure of the gel product to the heater 18. The gel container 17 may have three separate compartments. Each compartment is positioned between two bumps 35. The cover 11 is rotated to provide the desired strength by positioning the gel in increments adjacent the heater 18 with the bumps 35 providing an indication of the percentage strength in thirds. Of course other proportions could be utilized for control purposes but the foregoing division into thirds provides a noticeable regulation of the scent.

A dividing wall 21 separates the top half and the lower half of the cover 11. The height of the wall 21 is the distance between the base 14 and the inside roof of the cover 11. The wall 21 has several functions, namely it maintains the distance between the base 13 and cover 11 to accomodate the gel container 17. The wall 21 also keeps the heat or warm air away from the unused portion of the gel container 17 to prolong its useful life. Since warm air rises, the gel below the center line wall 21 will not be heated.

The dividing wall 21 also cooperates with the high bump 36 to provide a positive stop as the cover 12 is turned. For example, to load or unload the gel container 17, the cover 11 is turned counter clockwise until the right side of the wall 21 hits the high bump 36 on the base 13. On the other hand, turning the cover clockwise until the left side of the wall hits the high bump, means that all the compartments of the gel container 17 are exposed to the heated surface 18.

Openings 37 and 38 are provided in the cover and corresponding base sidewall 12 and 22 for loading and unloading of the gel container 17. The opening 37 is located on the lower left quarter portion of the cover side wall 12. The base sidewall 22 is raised in the upper half section to keep the gel container 17 inside the unit and cover-up the opening 37 for an improved aesthetic appearance. In a further embodiment the gel would be packaged in separate segments which would fit into individual compartments within the freshener which can be rotated opposite the heater. A degree of control could be imposed by the number of gel segments utilized.

Figure 8A:
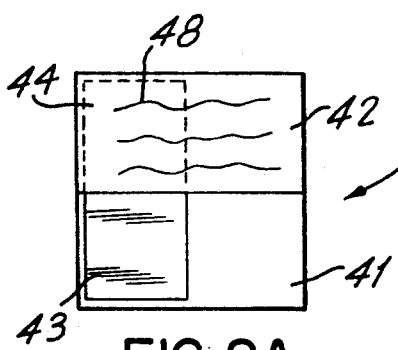
FIGS. 8A and 8B depict a slidable version of the invention showing a base and cover which cooperate to adjust the scent.
Figure 3:
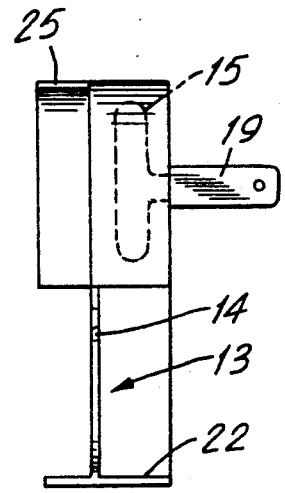
FIG. 3 is a crossectional view of the base.
Figure 8B:
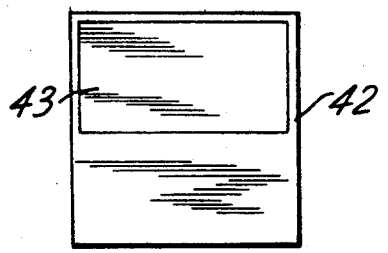

A further embodiment shown in FIGS. 8A,B to 9A,B shows a sliding adjustable design for the freshener 40. The freshener 40 is rectangular in design and includes a base 41 and a slidable cover 42 with apertures 43 therein. The cover 42 is moved with respect to the base 41 to provide an opening of a predetermined size to the heated gel 44. Raised portions can also be provided on the base 41 to indicate the amount of gel 44 exposed to the atmosphere and the heater 45.

While the invention has been explained by a detailed description of certain specific embodiments, it is understood that various modifications and substitutions can be made in any of them within the scope of the appended claims which are intended also to include equivalents of such embodiments.

What is claimed is:

1. An air freshener to dispense a predetermined amount of scent by heating a gel comprising:
    a base having a heater portion including an outwardly projecting connecting probe and a non-heater portion, wherein the base further includes three equal segments on the heater portion and bumps separating said segments, said heater and non-heater portions of the base each comprising half of the base,
    a cover rotatable about the base and having an upper portion with predetermined apertures therein, a transverse wall extending downwardly therefrom to engage the base and form a space between the heater and cover, and a downwardly extending peripheral wall having means at its lower end to engage and maintain the base in position, a gel mounted in the space between the heater portion and cover to provide a scent when heated through the apertures in the cover wherein said gel comprises a scented gel and a wrapping surrounding said gel in the shape of the segments for loading onto the base, and, wherein the cover is circular in configuration and the predetermined apertures comprise three spaced slots in the cover in the shape of arcs on one half of the circle and three uniform apertures forming sectors on the other half of the circle for rotation with the wrapped gel.

2. An air freshener in accordance with claim 1 wherein:

the base includes a plurality of raised radial bumps extending from the center of the base to the periphery and being spaced at predetermined intervals, on the heater portion, said bumps engaging the transverse wall of the cover to provide an indication of the cover rotation, and wherein the cover includes a solid upper portion and second portion having a plurality of apertures each corresponding to a bump, which are rotated with the gel to provide a predetermined amount of scent corresponding to the number of apertures positioned opposite the heater.

3. An air freshener in accordance with claim 1 wherein:

the cover includes at least one aperture in the peripheral wall and the base includes a wall extending upwardly at the periphery of the base having a loading aperture cooperating with the cover aperture to permit loading and unloading of the gel.

4. An air freshener in accordance with claim 1 wherein:

the cover further includes a solid upper portion having a plurality of spaced slots in the upper portion and a portion having a plurality of apertures for positioning adjacent the heater, and the base is colored so that the base is visible through the slots to provide an indication of the amount of scented gel exposed to the heater portion, and the base includes a raised radial bump between the solid upper portion and the portion with apertures, at one end which is engaged by the transverse wall to prevent further rotation of the cover.

5. An air freshener to dispense a predetermined amount of scent by heating a packaged gel comprising:

a rectangular base having a heater integrally mounted therein and an upper heater surface and a non-heater surface adjacent thereto and a peripheral wall extending upwardly and downwardly from the surfaces, a rectangular cover having downwardly extending peripheral sides to engage the peripheral wall of the base forming a compartment therebetween and said cover having a side aperture therein within which the base is slidable, and a scented gel being positioned on the non-heater surface, and wherein the base is slidable to position the gel adjacent predetermined positions of the heater to provide a selected strength of scent.

* * * * *